(12) United States Patent
Babaev (10) Patent No.: US 7,914,470 B2
(45) Date of Patent: *Mar. 29, 2011

(54) ULTRASONIC METHOD AND DEVICE FOR WOUND TREATMENT

(75) Inventor: Eilaz Babaev, Minnetonka, MN (US)

(73) Assignee: Celleration, Inc., Eden Prairie, MN (US)

( * ) Notice: Subject to any disclaimer, the term of this patent is extended or adjusted under 35 U.S.C. 154(b) by 1005 days.

This patent is subject to a terminal disclaimer.

(21) Appl. No.: 10/815,384

(22) Filed: Apr. 1, 2004

(65) Prior Publication Data

US 2004/0186384 A1    Sep. 23, 2004

Related U.S. Application Data

(63) Continuation-in-part of application No. 10/409,272, filed on Apr. 7, 2003, which is a continuation-in-part of application No. 09/669,312, filed on Sep. 25, 2000, now Pat. No. 6,569,099.

(51) Int. Cl.
- *A61H 1/00* (2006.01)
- *A61H 1/02* (2006.01)
- *A61H 5/00* (2006.01)
- *A61B 17/20* (2006.01)

(52) U.S. Cl. ......... 601/2; 604/22; 128/200.16; 600/439

(58) Field of Classification Search ............ 600/439, 600/437; 601/2, 3; 604/22; 128/200.14, 128/200.16; 239/102.2

See application file for complete search history.

(56) References Cited

U.S. PATENT DOCUMENTS

| | | | |
|---|---|---|---|
| 2,534,046 A | 12/1950 | Mau |
| 2,889,852 A | 6/1959 | Dunlap |
| 3,243,122 A | 3/1966 | Snaper |
| 3,275,059 A | 9/1966 | McCullough |
| 3,392,916 A | 7/1968 | Engstrom et al. |
| 3,433,226 A | 3/1969 | Boyd |
| 3,504,887 A | 4/1970 | Okerblom |
| 3,522,801 A | 8/1970 | Robinson |
| 3,561,444 A | 2/1971 | Boucher |
| 3,636,947 A | 1/1972 | Balamuth |
| 3,685,634 A | 8/1972 | Bergling |

(Continued)

FOREIGN PATENT DOCUMENTS

EP    0 020 844    10/1985

(Continued)

OTHER PUBLICATIONS

"Comparison Possibilities of Ultrasound and Its Combination with Laser in Surgery and Therapy".

(Continued)

*Primary Examiner* — Long V Le
*Assistant Examiner* — Jacqueline Cheng
(74) *Attorney, Agent, or Firm* — Patterson Thuente Christensen Pedersen, P.A.

(57) ABSTRACT

An apparatus and method are provided for applying a medicament to tissue, and delivering ultrasonic energy from a non-contact distance from the tissue to the medicament and to the tissue, wherein the ultrasonic energy has intensity capable of penetrating the wound tissue to a beneficial depth to provide a therapeutic effect to the tissue, and of sonicating the medicament for causing the medicament to penetrate the tissue to a beneficial depth to provide a therapeutic effect to the tissue.

47 Claims, 6 Drawing Sheets

U.S. PATENT DOCUMENTS

| | | |
|---|---|---|
| 3,765,606 A | 10/1973 | Moss et al. |
| 3,860,173 A | 1/1975 | Sata |
| 3,952,918 A | 4/1976 | Poitras et al. |
| 4,052,004 A | 10/1977 | Martin et al. |
| 4,085,893 A | 4/1978 | Durley, III |
| 4,153,201 A | 5/1979 | Berger et al. |
| 4,192,294 A | 3/1980 | Vasilevsky et al. |
| 4,251,031 A | 2/1981 | Martin et al. |
| 4,271,705 A | 6/1981 | Crostack |
| 4,294,407 A | 10/1981 | Reichl et al. |
| 4,301,093 A | 11/1981 | Eck |
| 4,301,968 A | 11/1981 | Berger et al. |
| 4,309,989 A | 1/1982 | Fahim |
| 4,319,155 A | 3/1982 | Nakai et al. |
| 4,334,531 A | 6/1982 | Reichl et al. |
| 4,352,459 A | 10/1982 | Berger et al. |
| 4,414,202 A | 11/1983 | Silvetti |
| 4,428,531 A | 1/1984 | Martin |
| 4,466,571 A | 8/1984 | Muhlbauer |
| 4,530,360 A | 7/1985 | Duarte |
| 4,541,564 A | 9/1985 | Berger et al. |
| 4,582,149 A | 4/1986 | Slaughter, Jr. |
| 4,582,654 A | 4/1986 | Karnicky et al. |
| 4,619,400 A | 10/1986 | Van Der Burgt |
| 4,642,581 A | 2/1987 | Erickson |
| 4,655,393 A | 4/1987 | Berger |
| 4,659,014 A | 4/1987 | Soth et al. |
| 4,679,551 A * | 7/1987 | Anthony ..................... 601/160 |
| 4,726,523 A | 2/1988 | Kokubo et al. |
| 4,726,525 A | 2/1988 | Yonekawa et al. |
| 4,733,820 A | 3/1988 | Endo et al. |
| 4,756,478 A | 7/1988 | Endo et al. |
| 4,767,402 A | 8/1988 | Kost et al. |
| 4,783,003 A | 11/1988 | Hirabayashi et al. |
| 4,790,479 A | 12/1988 | Matsumoto et al. |
| 4,793,339 A | 12/1988 | Matsumoto et al. |
| 4,818,697 A | 4/1989 | Liboff et al. |
| 4,850,534 A | 7/1989 | Takahashi et al. |
| 4,877,989 A | 10/1989 | Drews et al. |
| 4,883,045 A | 11/1989 | Theisz |
| 4,905,671 A | 3/1990 | Senge et al. |
| 4,930,700 A | 6/1990 | McKown |
| 4,941,618 A | 7/1990 | Hildebrand et al. |
| 4,961,885 A | 10/1990 | Avrahami et al. |
| 4,982,730 A | 1/1991 | Lewis, Jr. |
| 5,002,059 A | 3/1991 | Crowley et al. |
| 5,013,241 A | 5/1991 | von Gutfeld et al. |
| 5,040,537 A | 8/1991 | Katakura |
| 5,063,922 A | 11/1991 | Hakkinen |
| 5,076,266 A | 12/1991 | Babaev |
| 5,104,042 A | 4/1992 | McKown |
| 5,115,805 A | 5/1992 | Bommannan et al. |
| 5,134,993 A | 8/1992 | van der Linden et al. |
| 5,143,588 A | 9/1992 | Liboff et al. |
| 5,152,289 A | 10/1992 | Viebach et al. |
| 5,163,433 A | 11/1992 | Kagawa et al. |
| 5,172,692 A | 12/1992 | Kulow et al. |
| 5,186,162 A | 2/1993 | Talish et al. |
| 5,197,946 A | 3/1993 | Tachibana |
| 5,211,160 A | 5/1993 | Talish et al. |
| 5,219,401 A | 6/1993 | Cathignol et al. |
| 5,231,975 A | 8/1993 | Bommannan et al. |
| 5,259,384 A | 11/1993 | Kaufman et al. |
| 5,269,291 A | 12/1993 | Carter |
| 5,309,898 A | 5/1994 | Kaufman et al. |
| 5,314,441 A | 5/1994 | Cusack et al. |
| 5,315,998 A * | 5/1994 | Tachibana et al. ................. 601/2 |
| 5,316,000 A | 5/1994 | Chapelon et al. |
| 5,318,014 A | 6/1994 | Carter |
| 5,323,769 A | 6/1994 | Bommannan et al. |
| 5,324,255 A | 6/1994 | Passafaro et al. |
| 5,345,940 A | 9/1994 | Seward et al. |
| 5,347,998 A | 9/1994 | Hodson et al. |
| 5,362,309 A | 11/1994 | Carter |
| 5,374,266 A | 12/1994 | Kataoka et al. |
| 5,380,411 A | 1/1995 | Schlief |
| 5,393,296 A | 2/1995 | Rattner |
| 5,431,663 A | 7/1995 | Carter |
| 5,437,606 A | 8/1995 | Tsukamoto |
| 5,456,258 A | 10/1995 | Kondo et al. |
| 5,515,841 A | 5/1996 | Robertson et al. |
| 5,515,842 A | 5/1996 | Ramseyer et al. |
| 5,516,043 A | 5/1996 | Manna et al. |
| 5,520,166 A | 5/1996 | Ritson et al. |
| 5,520,612 A | 5/1996 | Winder et al. |
| 5,527,350 A | 6/1996 | Grove et al. |
| 5,529,572 A | 6/1996 | Spector |
| 5,545,124 A | 8/1996 | Krause et al. |
| 5,547,459 A | 8/1996 | Kaufman et al. |
| 5,551,416 A | 9/1996 | Stimpson et al. |
| 5,554,172 A | 9/1996 | Horner et al. |
| 5,556,372 A | 9/1996 | Talish et al. |
| 5,573,497 A | 11/1996 | Chapelon |
| 5,616,140 A | 4/1997 | Prescott |
| 5,618,275 A | 4/1997 | Bock |
| 5,626,554 A | 5/1997 | Ryaby et al. |
| 5,630,828 A | 5/1997 | Mawhirt et al. |
| 5,643,179 A | 7/1997 | Fujimoto |
| 5,656,016 A | 8/1997 | Ogden |
| 5,658,323 A | 8/1997 | Miller |
| 5,664,570 A | 9/1997 | Bishop |
| 5,688,224 A | 11/1997 | Forkey et al. |
| 5,699,805 A | 12/1997 | Seward et al. |
| 5,707,402 A | 1/1998 | Heim |
| 5,707,403 A | 1/1998 | Grove et al. |
| 5,725,494 A | 3/1998 | Brisken |
| 5,730,705 A | 3/1998 | Talish et al. |
| 5,735,811 A | 4/1998 | Brisken |
| 5,743,863 A | 4/1998 | Chapelon |
| 5,752,924 A | 5/1998 | Kaufman et al. |
| 5,762,616 A | 6/1998 | Talish |
| 5,785,972 A | 7/1998 | Tyler |
| 5,835,678 A | 11/1998 | Li et al. |
| 5,843,139 A | 12/1998 | Goedeke et al. |
| 5,879,314 A | 3/1999 | Peterson et al. |
| 5,879,364 A | 3/1999 | Bromfield et al. |
| 5,882,302 A | 3/1999 | Driscoll, Jr. et al. |
| 5,894,841 A | 4/1999 | Voges |
| 5,895,362 A | 4/1999 | Elmstrom et al. |
| 5,904,659 A | 5/1999 | Duarte et al. |
| 5,947,921 A | 9/1999 | Johnson et al. |
| 5,960,792 A | 10/1999 | Lloyd et al. |
| 5,989,245 A | 11/1999 | Prescott |
| 6,001,069 A | 12/1999 | Tachibana et al. |
| 6,007,499 A | 12/1999 | Martin et al. |
| 6,014,970 A | 1/2000 | Irvi et al. |
| 6,024,718 A | 2/2000 | Chen et al. |
| 6,026,808 A | 2/2000 | Armer et al. |
| 6,027,495 A | 2/2000 | Miller |
| 6,036,661 A | 3/2000 | Schwarze et al. |
| 6,041,253 A * | 3/2000 | Kost et al. ..................... 604/20 |
| 6,061,597 A | 5/2000 | Rieman et al. |
| 6,076,519 A | 6/2000 | Johnson |
| 6,083,159 A | 7/2000 | Driscoll, Jr. et al. |
| 6,095,141 A | 8/2000 | Armer et al. |
| 6,098,620 A | 8/2000 | Lloyd et al. |
| 6,102,298 A | 8/2000 | Bush et al. |
| 6,104,952 A | 8/2000 | Tu et al. |
| 6,106,547 A | 8/2000 | Huei-Jung |
| 6,113,558 A | 9/2000 | Rosenschein et al. |
| 6,113,570 A | 9/2000 | Siegel et al. |
| RE36,939 E | 10/2000 | Tachibana et al. |
| 6,158,388 A | 12/2000 | Wenstrand |
| 6,158,431 A | 12/2000 | Poole |
| 6,161,536 A | 12/2000 | Redmon et al. |
| 6,176,839 B1 | 1/2001 | Deluis et al. |
| 6,186,963 B1 | 2/2001 | Schwarze et al. |
| 6,190,315 B1 | 2/2001 | Kost et al. |
| 6,190,336 B1 | 2/2001 | Duarte et al. |
| 6,206,842 B1 | 3/2001 | Tu et al. |
| 6,206,843 B1 | 3/2001 | Iger et al. |
| 6,231,528 B1 | 5/2001 | Kaufman et al. |
| 6,234,990 B1 | 5/2001 | Rowe et al. |
| 6,251,099 B1 | 6/2001 | Kollias et al. |
| 6,254,294 B1 | 7/2001 | Muhar |
| 6,273,864 B1 * | 8/2001 | Duarte et al. ..................... 601/2 |
| 6,296,630 B1 | 10/2001 | Altman et al. |

| | | | |
|---|---|---|---|
| 6,311,573 B1 | 11/2001 | Bhardwaj | |
| 6,314,318 B1 | 11/2001 | Petty | |
| 6,321,109 B2 | 11/2001 | Ben-Haim et al. | |
| 6,322,527 B1 | 11/2001 | Talish | |
| 6,325,769 B1 | 12/2001 | Klopotek | |
| 6,458,109 B1 * | 10/2002 | Henley et al. | 604/304 |
| 6,478,754 B1 * | 11/2002 | Babaev | 601/2 |
| 6,500,133 B2 * | 12/2002 | Martin et al. | 601/3 |
| 6,533,484 B1 | 3/2003 | Osei et al. | |
| 6,533,803 B2 | 3/2003 | Babaev | |
| 6,559,365 B2 | 5/2003 | Wilfer | |
| 6,569,099 B1 * | 5/2003 | Babaev | 600/439 |
| 6,583,071 B1 | 6/2003 | Weidman et al. | |
| 6,601,581 B1 | 8/2003 | Babaev | |
| 6,623,444 B2 | 9/2003 | Babaev | |
| 6,659,365 B2 | 12/2003 | Gipson et al. | |
| 6,663,554 B2 * | 12/2003 | Babaev | 600/2 |
| 6,666,431 B2 | 12/2003 | McCusker | |
| 6,723,064 B2 | 4/2004 | Babaev | |
| 6,732,744 B2 | 5/2004 | Olshavsky et al. | |
| 6,761,729 B2 | 7/2004 | Babaev | |
| 6,916,296 B2 * | 7/2005 | Soring et al. | 601/2 |
| 6,919,296 B2 | 7/2005 | Geus et al. | |
| 6,960,173 B2 | 11/2005 | Babaev | |
| 6,964,647 B1 | 11/2005 | Babaev | |
| 7,316,664 B2 | 1/2008 | Kadziauskas et al. | |
| 2002/0062093 A1 | 5/2002 | Soring et al. | |
| 2002/0080206 A1 | 6/2002 | Lin | |
| 2002/0138036 A1 | 9/2002 | Babaev | |
| 2002/0177846 A1 * | 11/2002 | Mulier et al. | 606/27 |
| 2003/0023193 A1 | 1/2003 | Soring et al. | |
| 2003/0125660 A1 | 7/2003 | Moutafis et al. | |
| 2003/0195644 A1 | 10/2003 | Borders et al. | |
| 2003/0236560 A1 | 12/2003 | Babaev | |
| 2004/0028552 A1 | 2/2004 | Bhardwaj et al. | |
| 2004/0030254 A1 | 2/2004 | Babaev | |
| 2004/0034982 A1 | 2/2004 | Wieber et al. | |
| 2004/0055376 A1 | 3/2004 | Thompson et al. | |
| 2004/0076175 A1 | 4/2004 | Patenaude | |
| 2005/0075620 A1 | 4/2005 | Iger | |
| 2006/0025716 A1 | 2/2006 | Babaev | |
| 2006/0058710 A1 | 3/2006 | Babaev | |
| 2007/0016110 A1 | 1/2007 | Babaev et al. | |
| 2007/0088245 A1 | 4/2007 | Babaev et al. | |
| 2008/0177221 A1 | 7/2008 | Millerd et al. | |
| 2008/0214965 A1 | 9/2008 | Peterson et al. | |
| 2009/0043248 A1 | 2/2009 | Peterson | |

FOREIGN PATENT DOCUMENTS

| | | |
|---|---|---|
| EP | 0 437 155 B1 | 2/1990 |
| EP | 0416106 A1 | 3/1991 |
| EP | 0 657 226 B1 | 11/1994 |
| EP | 0 619 104 | 3/2002 |
| EP | 1 564 009 | 8/2005 |
| GB | 2099710 A | 12/1982 |
| GB | 2101500 A | 1/1983 |
| JP | 417844 | 1/1992 |
| JP | 09135908 A | 5/1997 |
| JP | 2000237275 | 9/2000 |
| SU | 878268 | 11/1981 |
| SU | 910157 B | 3/1982 |
| SU | 1106485 A | 10/1982 |
| SU | 1106485 A * | 8/1984 |
| SU | 1827239 | 5/1990 |
| WO | WO 94/06380 | 3/1994 |
| WO | WO 96/35383 | 11/1996 |
| WO | 97/17933 | 5/1997 |
| WO | WO 02/24150 A2 | 1/2002 |
| WO | 02/24150 A2 | 3/2002 |
| WO | WO 02/28350 A2 | 4/2002 |
| WO | 02/055131 A2 | 7/2002 |
| WO | 02/060525 A2 | 8/2002 |

OTHER PUBLICATIONS

Zharov et al, pp. 331-339, In Biomedical Optoacoustics.
European Search Report dated Sep. 13, 2004.
International Search Report dated Oct. 1, 2004.
XP-002294548, Abstract corresponding to SU 914099.
U.S. Appl. No. 10/409,272, filed Apr. 7, 2003, Babaev.
U.S. Appl. No. 90/007,613, filed Jul. 5, 2005, Babaev.
Ennis W.J., et al., "Ultrasound Therapy for Recalcitrant Diabetic Foot Ulcers: Results of a Randomized, Double-Bind, Controlled, Multicenter Study," Ostomy/Wound Management, 2005; 51(8): pp. 24-39.
Image File Wrapper for U.S. Appl. No. 11/473,934; filed Jun. 23, 2006.
Iraniha S., et al. "Determination of Burn Depth With Noncontact Ultrasonography," Journal of Burn Care Rehabilitation (2000)21: pp. 333-338.
Department of Health & Human Services Letter dated Jun. 25, 2004 (3 pages).
Department of Health and Human Services Letter dated May 17, 2005 (3 pages).
Image File Wrapper for U.S. Appl. No. 09/669,312; filed Jan. 12, 2001.
Image File Wrapper for U.S. Appl. No. 10/409,272; filed Apr. 7, 2003.
Image File Wrapper for U.S. Appl. No. 10/815,384; filed Apr. 1, 2004.
Image File Wrapper for U.S. Appl. No. 09/774,145; filed Jan. 30, 2001.
Image File Wrapper for U.S. Appl. No. 09/684,044; filed Oct. 6, 2002.
Image File Wrapper for U.S. Appl. No. 11/207,334; filed Aug. 18, 2005.
Image File Wrapper for U.S. Appl. No. 11/232,801; filed Sep. 22, 2005.
Image File Wrapper for U.S. Appl. No. 11/168,620; filed Jun. 27, 2005.
Image File Wrapper for U.S. Appl. No. 11/473,934; filed Jun. 23, 2006.
Image File Wrapper for U.S. Appl. No. 12/006,739; filed Jan. 4, 2008.
Image File Wrapper for U.S. Appl. No. 12/218,760; filed Jul. 17, 2008.

* cited by examiner

ULTRASONIC METHOD AND DEVICE FOR WOUND TREATMENT

This application is a Continuation-In-Part of U.S. application Ser. No. 10/409,272 filed on Apr. 7, 2003, by Eilaz Babaev, entitled: ULTRASONIC METHOD AND DEVICE FOR WOUND TREATMENT, which is a Continuation-In-Part of U.S. application Ser. No. 09/669,312 filed on Sep. 25, 2000, by Eilaz Babaev, now U.S. Pat. No. 6,569,099, entitled: ULTRASONIC METHOD AND DEVICE FOR WOUND TREATMENT, the entire contents of both applications are hereby incorporated by reference.

FIELD OF THE INVENTION

The present invention relates to methods of using ultrasonic waves in wound treatment. More particularly, the present invention relates to a method of applying a medicament to tissue and delivering ultrasound energy to the medicament and the tissue.

BACKGROUND OF THE INVENTION

Ultrasonic waves have been widely used in medical applications, including for both diagnostics and therapy as well as for many industrial applications. One diagnostic use of ultrasound waves includes using ultrasonic waves to detect underlying structures in an object or a human tissue. In this procedure, an ultrasonic transducer is placed in contact with the object or tissue via a coupling medium, and high frequency (1-10 MHz) ultrasonic waves are directed into the tissue. Upon contact with various underlying structures, the waves are reflected back to a receiver adjacent the transducer. By comparison of the signals of the ultrasonic wave as sent with the reflected ultrasonic wave as received, an image of the underlying structure can be produced. This technique is particularly useful for identifying boundaries between components of tissue and can be used to detect irregular masses, tumors, and the like.

Two therapeutic medical uses of ultrasound waves include aerosol mist production and contact physiotherapy. Aerosol mist production makes use of a nebulizer or inhaler to produce an aerosol mist for creating a humid environment and delivering drugs to the lungs. Ultrasonic nebulizers operate by the passage of ultrasound waves of sufficient intensity through a liquid, the waves being directed at an air-liquid interface of the liquid at a point underneath or within the liquid. Liquid particles are ejected from the surface of the liquid into the surrounding air following the disintegration of capillary waves produced by the ultrasound energy. This technique can produce a very fine dense fog or mist. Aerosol mists produced by ultrasound are preferred over aerosol mists produced by other methods because a smaller particle size of aerosol can be obtained with the ultrasonic waves. One of the major shortcoming of inhalers and nebulizers is that the aerosol mist cannot be directed to a target area without an air stream, which decreases the efficiency of the ultrasound energy. Ultrasonic sprayers such as those sold by Sonic and Materials Inc., Misonix Inc., Sono-Tek Inc. (see, for example, U.S. Pat. Nos. 4,153,201, 4,655,393, and 5,516,043) operate by passing liquid through a central orifice of an ultrasound instrument-tip. Major disadvantages of these sprayers include non-uniform particle size, heating of liquid flow, and less efficiency of ultrasound waves because of a demolished end (radiation) surface configuration of the tip.

Contact physiotherapy applies ultrasonic waves directly to tissue in an attempt to produce a physical change in the tissue. In conventional ultrasound physiotherapy, an ultrasonic wave contacts the tissue via a coupling medium. Ultrasonic waves produced by the transducer travel through the coupling medium and into the tissue. The coupling medium is typically a bath of liquid, a jelly applied to the surface to be treated, or a water-filled balloon. Conventional techniques provide ultrasonic waves having an intensity of about 0.1 w/cm$^2$ to 3 w/cm$^2$ at a frequency of about 0.8 to 3 Megahertz. The treatment is applied to a skin surface for from about 1 to 30 minutes, two or three times a week. The coupling medium can provide a cooling effect which dissipates some of the energy produced by the ultrasonic transducer.

More importantly, a coupling medium or direct contact between the tissue and ultrasonic transducer is necessary to transmit the ultrasonic waves to the skin surface because ambient air is a relatively poor medium for the propagation of ultrasonic waves.

Several beneficial effects have been reported from contact ultrasound physiotherapy, such as, for example, the following: local improvement of the blood circulation, heating of the tissue, accelerated enzyme activity, muscle relaxation, pain reduction, and enhancement of natural healing processes. Despite these beneficial effects, current techniques of medical physiotherapy using ultrasonic waves are limited by the necessity of providing a direct contact interface between the ultrasonic transducer and the tissue to maintain an effective transmission of the ultrasonic waves from the transducer to the tissue.

The necessity of direct contact with or without a coupling medium makes current methods undesirable. Some tissue conditions may be accessible to contact ultrasound devices but would be impractical for contact ultrasound treatment. For example, fresh or open wounds resulting from trauma, burns or surgical interventions are not suitable for direct contact ultrasound treatment because of the structural nature of the open wound and the painful condition associated with those wounds. Moreover, conventional contact ultrasound may have a destructive effect on these types of open wounds due to the close proximity of an oscillating tip of an ultrasonic transducer relative to the already damaged tissue surface.

OBJECT OF THE INVENTION

It is an object of the invention to provide an improved method and device for treating tissue.

It is also an object of this invention to provide a method and device for treating tissue using ultrasonic waves.

It is a further object of the invention to provide a method and device for delivering drugs, killing bacteria, cleansing a surface, or stimulating healthy tissue cell growth.

It is a yet further object of the invention to treat a wound by spraying the surface of the wound with aerosol mist produced by ultrasonic waves.

It is also an object of the invention to provide a method and device for applying a medicament to the tissue before and/or during delivery of ultrasound energy to the tissue.

These and other objects of the invention will become more apparent from the discussion below.

SUMMARY OF THE INVENTION

The present invention provides an apparatus and a method for treating tissue, the apparatus including a generator and a transducer for generating ultrasonic energy and delivering the ultrasonic energy to the biological tissue, from a non-contact distance from the tissue, wherein the generated ultrasonic energy has an intensity capable of penetrating the wound tissue to a beneficial depth to provide a therapeutic effect to the tissue, and of sonicating the medicament for causing the medicament to penetrate the tissue to a beneficial depth to provide a therapeutic effect to the tissue.

The present invention further provides an apparatus and method for generating ultrasonic energy from a non-contact distance from the surface of the wound; and delivering the generated ultrasonic energy to the wound through a gaseous medium ("dry" approach), wherein the generated ultrasonic energy has an intensity capable of penetrating the wound tissue to a beneficial depth to provide a therapeutic effect for decreasing the healing time for the wound.

The present invention further relates to a method and device for spraying ("wet" approach) a wound surface to deliver drugs, kill bacteria, or cleanse a surface by non-contact application of an ultrasound transducer tip. The method applies ultrasonic waves to the wound without requiring direct or indirect (via a traditional coupling medium) contact between the ultrasonic wave transducer and the wound to be sprayed.

The method of the invention comprises producing a directed spray of liquid or powder particles produced by contact of the liquid or powder with a free end surface of an ultrasonic transducer. The ultrasonic waves cause the spray to project outwardly from the distal end surface of the ultrasonic transducer, and the particle spray is directed onto the wound. The particles of the spray provide a medium for propagation of the ultrasonic waves emanating from the distal end surface. According to the method of the present invention a directed particle spray created by low frequency ultrasound waves onto a wound, delivers drug, kills bacteria on the wound, increases blood flow, and removes dirt and other contaminants from the wound's surface (mechanical cleansing).

This method of drug delivery is particularly advantageous on tissues for which local topical application of a drug is desirable but contact with the tissue is to be avoided. Furthermore, the low frequency ultrasound waves used in the method energize the drug and cause penetration of the drug below the surface of the tissue, due to acoustic pressure, microcavitation, etc. Finally, the bacteria killing method is effective when applied to the surface whether the liquid or powder sprayed is a drug (an antiseptic or antibiotic), oil, saline, distilled water, etc.

DETAILED DESCRIPTION OF THE INVENTION

The device of the invention that produces a spray is characterized by means for first delivering the liquid to a lateral surface of an ultrasonic transducer tip adjacent to a free end surface such that the liquid is pulled to the free end surface by a vacuum (negative pressure) created by the ultrasound waves on the free end surface of the transducer tip. This effect can be achieved while the angle between the ultrasound instrument and the horizontal is modified up to 90°. (This acoustical effect of delivering liquid from radial side of a tip to the free end was discovered by the inventor of this invention and is called the "Babaev effect".) This effect occurs when liquid is delivered to the radial surface of a transducer tip about its perimeter, up to 360° about its perimeter, e.g. from the top, side, bottom, etc.

For the above purpose the device preferably has a so-called nozzle constructed from steel (non-disposable) or plastic (disposable) with a suitable valve design. The nozzle allows delivery of liquid to the lateral surface of the transducer tip or directly to the distal side (radiation surface) of the ultrasound transducer, for enabling the transducer to act as a sprayer or atomizer.

One of the major advantages of the invention is the uniformity of the spray particles generated. Because liquid or powder is sprayed from a solid radiation surface, there is substantial uniformity of particle size, about 90% or greater, preferably from about 90 to 96%. It is provided that the distal radiation surface is driven with constant frequency and amplitude to create the spray. It is also provided that the frequency and/or amplitude can be modulated during treatment and that the distal radiation surface is driven with a sinusoidal, rectangular, trapezoidal or triangular wave form.

The step of producing the spray can further include operating the transducer to produce ultrasonic waves having a frequency of from about 18 kHz to 10,000 MHz. Frequencies below 18 kHz, i.e., from about 1 to 18 kHz, can be used as well; however, this lower range is less desirable because this range of sound wave can be uncomfortable to the patient and operator (without ear protection or the like). Frequencies in the range of from about 30 to 100 kHz are preferred, and frequencies of about 40 kHz are most preferred.

The separation distance between the free end surface of the transducer and the surface or object to be sprayed should be a "non-contact" distance of at least 0.1 in. (2.5 mm). Preferably the separation distance is from about 0.1 in. (2.5 mm) to 20 in. (51 cm), more preferably from about 0.1 in. (2.5 mm) to 5 in. (12.7 cm). The liquid or powder to be sprayed can be any appropriate carrier such as water (regular or distilled), saline solution, or oil to be applied to tissue (i.e., biological tissue or non-biological tissue), such as a vegetable, peanut, or canola oil, optionally with a soluble pharmaceutical, e.g., an antibiotic, antiseptic, conditioner, surfactant, emollient, or other active ingredient. The pharmaceutical or the like is preferably present in a concentration sufficiently low to be soluble but high enough to be effective for the intended purpose.

It is within the scope of the invention that the liquid to be sprayed could include a mixture of two or more immiscible liquids or a heterogeneous mixture of a solution and small particles. It is also within the scope of the invention that the spray could include particles, such as powder, and that the liquid in the reservoir could include powder.

The spray produced according to the invention is directed to the object, surface, or tissue to be sprayed for the time and frequency required for accomplishing a particular purpose or treatment. It is believed that a minimum length of spray of at least one second will be required; however, the length or duration of the spray could be from about one second to as much as a minute or more, even 30 minutes. Numerous factors or circumstances, such as, for example, the area to be sprayed (e.g., the size of a wound), the volume rate of spray produced, the concentration of active ingredient, etc., will impact upon the duration and/or frequency of the spraying. Spraying could be required from one or more times daily to as little as two or three times a week or month.

According to the invention, ultrasonic waves are applied to a wound without establishing contact, directly or indirectly, between the ultrasonic transducer and the wound. For example, surfaces of the human body especially suited for treatment in accordance with the method of the present invention include infected and inflammatory situations in open wounds, including trauma or gun shut wounds, fire and chemical burns.

In addition, the method of the present invention is particularly suited to directing a spray into orifices or other body crevices that are difficult to access.

Wound treatment according to the method and apparatus of the present invention has several advantages. First, this method topically applies medicines such as liquid antibiotics to the wound surface without the need to contact infected, inflamed or painful tissue with an instrument. And second, a significant bactericidal effect occurs when a wound surface is sprayed using the method of the present invention.

Moreover, aside from the bactericidal effect and advantages of non-contact treatment, it has been found that using the method of the present invention gave a significant reduction in volume used of liquid medicine used as compared with traditional methods for wound treatment. Similarly, this allows for precise dosage of the sprayed liquid to permit a user, such as a physician, to administer the desired volume of liquid at a desired rate and duration.

It has been found that the method of the present invention decreases healing times for inflammatory and purulent infected wounds from about 1.5 to 3 times faster than traditional methods. This effect results from a bactericidal, blood flow increasing and mechanical cleansing effect of the atomized spray particles, which have ultrasound energy due to the ultrasonic waves. The spray mechanically scrubs the surface of tissue to remove dirt, dead tissue, and purulent buildup on the tissue surface. The mentioned healing effect also results of energized and highly activated antibiotics, and drug penetration into the tissue surface up to 0.5 mm in depth under influence of ultrasound waves.

Additionally, a combination of the low frequency ultrasonic waves and the sonicated medicines (highly activated by ultrasonic energy) destroys the surface bacteria, resulting in a higher disinfecting property of sonicated liquids as compared to ordinarily applied liquids.

The spray of the present method also stimulates healthy cell growth to aid in granulation and epithelization of the healing tissue.

Other applications of the invention can be directed to non-medical uses such as cleansing, sterilizing and coating surfaces of objects and food.

The method of the present invention offers an approach that may re-establish use of some traditional antibiotics and establish a method for fighting bacteria without antibiotics when necessary. The effect of the method of the present invention in highly activating antibiotics may allow some traditional antibiotics to overcome bacteria which have become resistant to that antibiotic. Moreover, independent of the sonication effect of the antibiotics, the low frequency ultrasonic waves applied in accordance with the method of the present invention physically destroy bacteria. The combination of the highly activated antibiotics and of the low frequency ultrasonic waves in accordance with the method of the present invention produce a strong bactericidal effect not found in mere topical application or oral ingestion of antibiotics. This combined effect has been shown to significantly increase the healing of purulent infected wounds.

The present method also provides a system of non-contact drug delivery without use of a compression sprayer system. This simplifies the design of a non-contact drug delivery sprayer and reduces the weight of the sprayer. More importantly, not using compression to propel the atomized particles preserves the ultrasound energy carried by the spray particles.

Delivery of ultrasound energy in accordance with the present invention has been proven to destroy bacteria by action of the ultrasonic waves and by highly activated liquid medicines applied to the tissue.

The method of the present invention provides a method of compressionless non-contact drug delivery.

Figure 1:
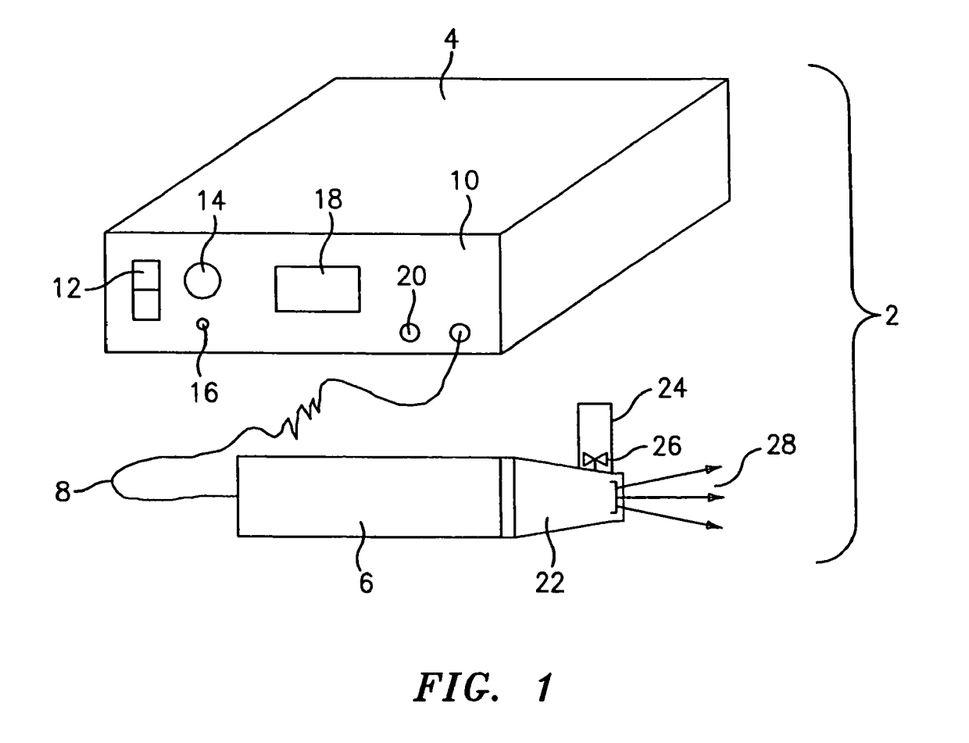
FIG. 1 is a perspective view of an ultrasonic wound treatment system according to the present invention.

The invention is better appreciated by making reference to the drawings. In FIG. 1, an ultrasonic treatment system 2 includes an ultrasound generator 4, connected to an ultrasound transducer 6 by a cable 8. The generator 4, which is conventional, may have a front panel 10 with a power button 12, a timer 14, a control button 16, a display 18, and one or more jacks 20, for example, for connecting a footswitch. A nozzle 22 having a liquid reservoir 24 with a valve 26 is attached to the distal portion of transducer 6. Arrows 28 represent the direction of the spray produced.

Figure 2:
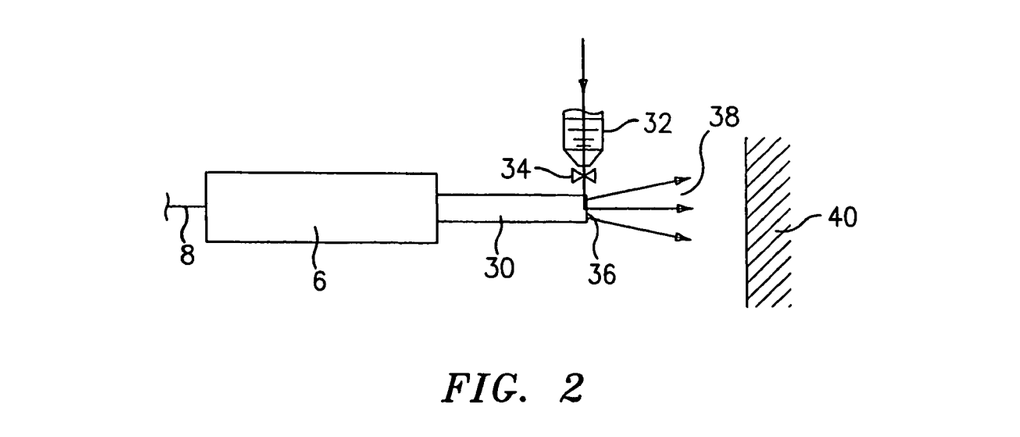
FIG. 2 is a lateral schematic view of an ultrasonic sprayer according to the present invention.
Figure 3:
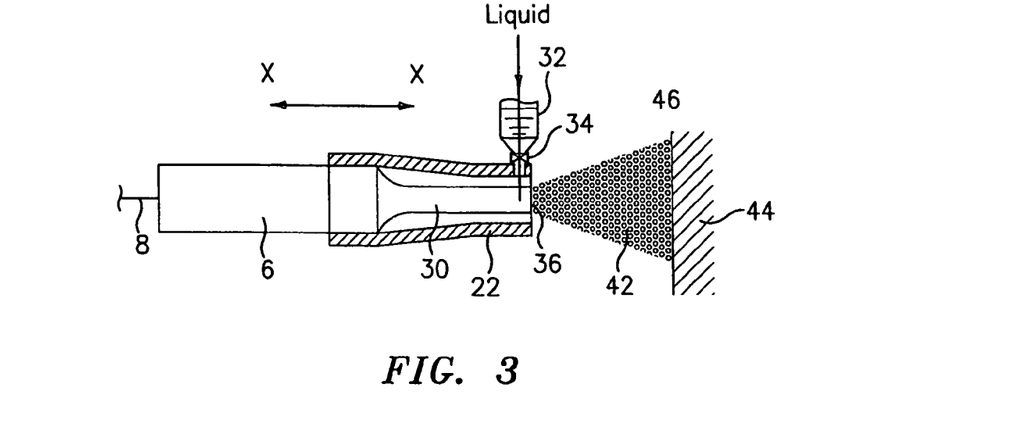
FIG. 3 is a partly cross-sectional view of an ultrasonic sprayer according to the present invention.

FIG. 2 is a simplified representation of an ultrasonic device and spray according to the invention. Transducer 6 has a distal transducer tip or horn 30. Liquid from a liquid reservoir 32 flows through a valve 34 to a position adjacent the distal radiation surface 36 of a horn 30. Transducer 6 is attached to an ultrasound source via cable 8. A liquid mist is directed in the direction of arrows 38 to target tissue or surface 40 (wet approach).

FIG. 3 is an enlarged, partly cross-sectional view of a section of FIG. 1 illustrating a spray created by the device according to the method of the present invention. This device is a modification and implementation of a device disclosed in U.S. Pat. No. 5,076,266, which is incorporated herein by reference. As can be seen in more detail in FIG. 3, nozzle 22 surrounds ultrasound horn 30. Also, liquid reservoir 32 has a valve 34 positioned between reservoir 32 and the distal surface 36 of ultrasonic horn 30. A conical spray pattern of liquid particles 42 is directed at a surface or tissue 44 of a target. This configuration is effective to spray liquid onto a surface and to deliver ultrasonic waves to that surface, such as, for example, the surface of a wound.

Valve 34 allows liquid to flow to distal tip 36 as drops or as a continuous flow through gap 46. Valve 34 may be located anywhere, including between reservoir 32 and horn 30. Mechanical movement of the horn 30 in the direction x-x causes liquid to flow to the distal end of radiation surface 36.

Figure 4A:
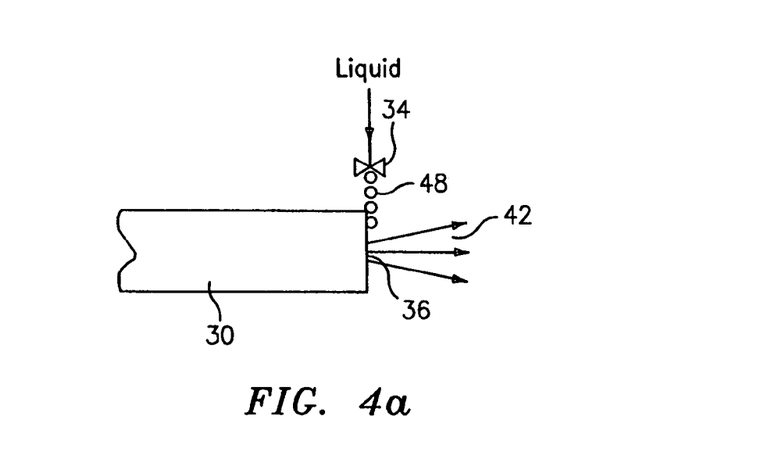
FIG. 4a is a detailed view of the sprayer illustrated in FIG. 3 for spraying liquid from a radiation surface.

FIG. 4(*a*) is a view of the ultrasonic sprayer as used in accordance with the method of the present invention for spraying liquid 48 directed to distal end (radiation surface) 36.

Figure 4B:
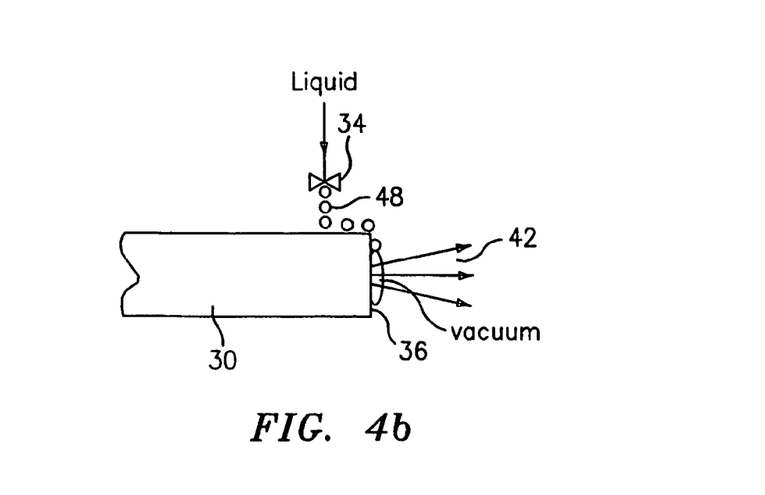
FIG. 4b is a detailed view of the sprayer illustrated in FIG. 3 for spraying liquid from a side (radial) surface.

FIG. 4(*b*) is a view of the basic spraying method from side (radial) surface of the tip based on the Babaev effect. In this example, liquid or drug directed to the radiation surface 36 of ultrasound horn 30 becomes sonicated (ultrasonically energized), after being pulled forward by negative pressure (vacuum) created by ultrasound waves and sprays.

Figures 5, 6:
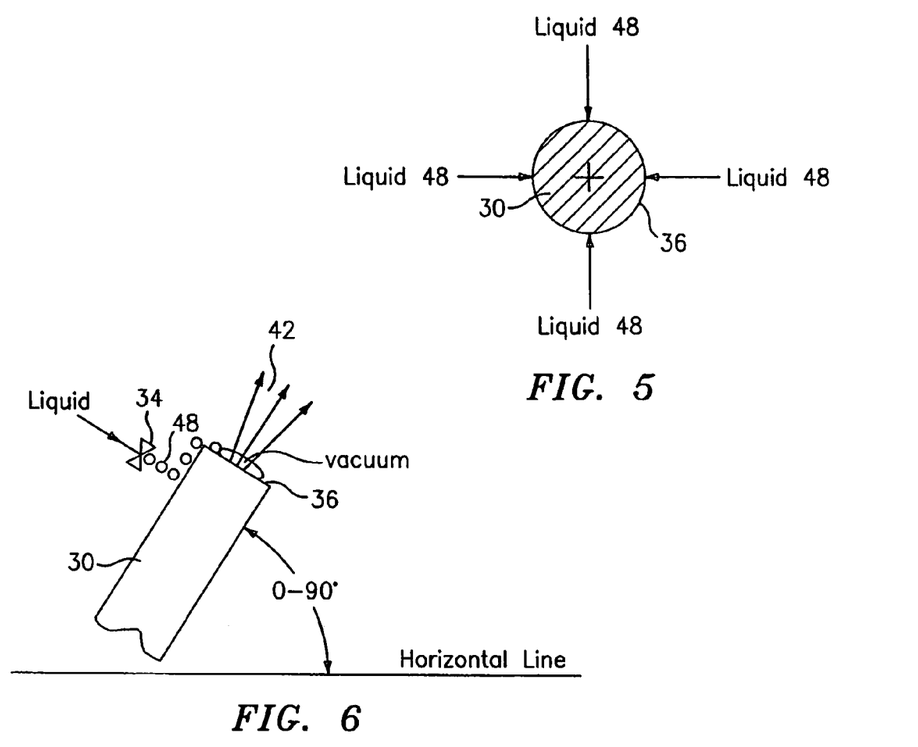
FIG. 5 is a cross-sectional front view of a distal end of an ultrasonic transducer when liquid is delivered to the side or radiation surface of the transducer tip from 360° along its perimeter.
FIG. 6 is a variation of FIG. 4b illustrating the spraying effect by changing the angle between the ultrasound instrument and horizontal line from 0° to 90°.
Figure 7A:
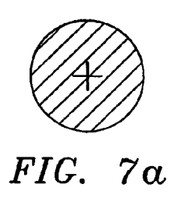
FIGS. 7a-7g are each a front cross-sectional view of an ultrasound tip configuration.
Figure 7B:
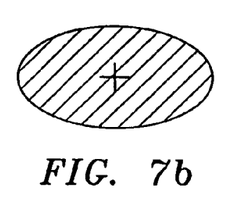
Figure 7C:
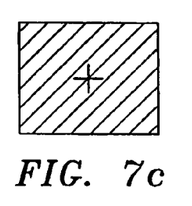
Figure 7D:
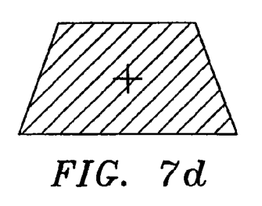
Figure 7E:
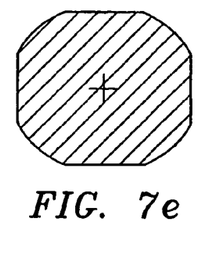
Figure 7F:
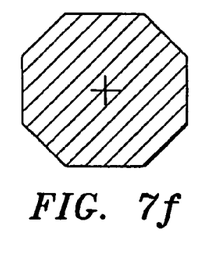
Figure 7G:
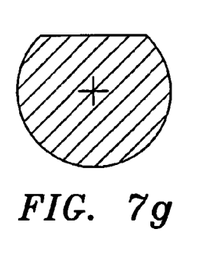
Figure 8A:
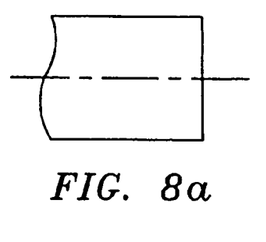
FIGS. 8a-8i are each an enlarged side view of a different modification of a tip end shape of the ultrasonic sprayer according to the present invention.
Figure 8B:
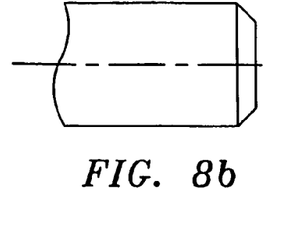
Figure 8C:
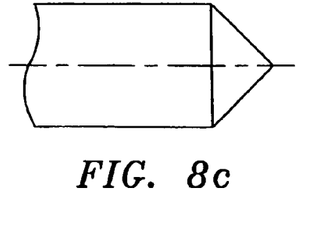
Figure 8D:
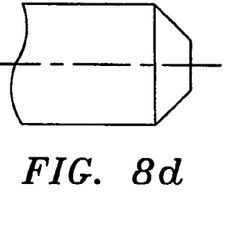
Figure 8E:
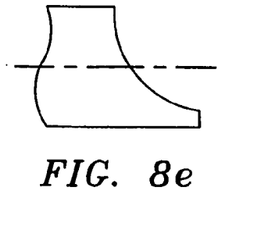
Figure 8F:
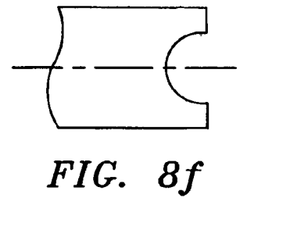
Figure 8G:
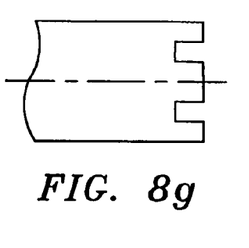
Figure 8H:
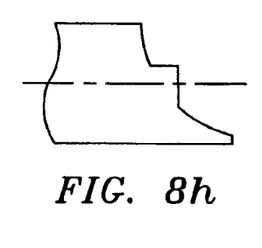
Figure 8I:
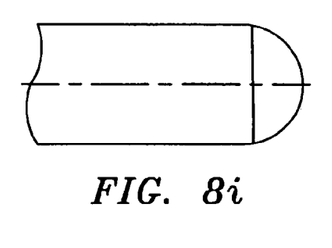

As shown in FIG. 5, liquid is delivered to the side of radiation surface 36 of transducer horn 30 about the perimeter of radiation surface 36, up to 360° about its perimeter, e.g. from the top, side, bottom, etc.

In the embodiment of the invention shown in FIG. 6, a partial section of transducer horn 30 is elevated from the horizontal up to 90°. Due to the Babaev effect, liquid 48 still travels to radiation surface 36.

The ultrasound tip or horn may have a regular or irregular lateral cross-section, including circular, oval, elliptical, rectangular, trapezoidal, or a combination thereof. For example, FIGS. 7(*a*) to 7(*g*) are each a view of a cross-section of an ultrasound tip or horn. Also, the distal end shape of the ultrasound tip or horn longitudinal cross-section may vary, and may be rectangular, elliptical, oval, spherical, conical, curved, stepped, with chamfer, etc., as shown in FIGS. 8(*a*) to 8(*n*), which are each an enlarged view in section of a different, exemplary modification of a tip of the sprayer as used in accordance with the method of the present invention. The preferred shape is rectangular, because radiation beams from ultrasound tip surface are substantially fully directed to the target (wound). With the spherical, elliptic and oval (FIG. 8(*e*)) form or shape of the distal end, radiation beams are focused at a focal point. However, with other forms or shapes of the distal end, radiation beams are spread, thus partially reaching the target.

Figure 9A:
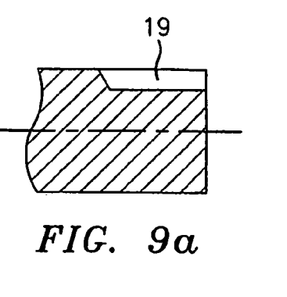
FIGS. 9a, 9b, and 9c represent cross-sectional, distal, and lateral views, respectively, of the top of an ultrasonic sprayer having a slot, groove, or thread.
Figure 9B:
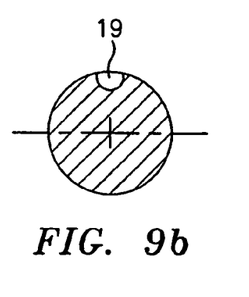
Figure 9C:
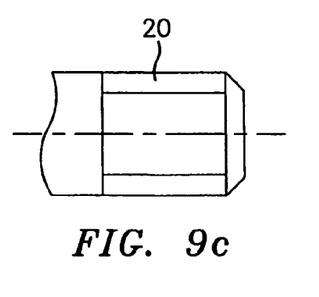

Radial side surface of the distal end of the tip may have a slot (groove) or thread for liquid to be directed to the radiation surface (FIGS. 9*a*-9*c*).

FIGS. 9*a* to 9*c* are each a view of a radial side surface of the distal end of the tip which has a slot (groove) 19 or thread 20 for liquid to be directed to the radiation surface.

The ultrasonic energy delivered has an intensity capable of providing a therapeutic effect to the wound 40, exerting acoustic pressure and/or causing micro-cavitation. Acoustic pressure refers to a force that can be felt which is exerted through air between the transducer and the tissue being targeted. Microcavitation refers to the formation and pulsation of gas or vapor filled microscopic bubbles in fluids as a result of ultrasonically induced and regularly repeated pressure changes. Advantages to microcavitation include the creation of acoustic streaming which is a steady circulation of fluid in blood vessels induced by ultrasound radiation force.

Preferably, the amplitude achieved by the ultrasonic energy is at least 3 microns and preferably at least 10 microns. Preferably, the frequency used is in the range of 20 kHz-50 MHz, wherein a preferred range is 20-200 kHz, a more preferred range is 20-40 kHz and a most preferred value is 40 kHz, wherein most preferably the lower limit of the frequency used is outside of the human hearing range.

Furthermore, it is advantageous to use a radiation surface 36 having a shape and size selected to achieve delivery of the ultrasonic energy to the wound where the delivered ultrasonic energy has an intensity capable of providing a therapeutic effect to the wound. Selection of the shape and size of the radiation surface 36 in combination with selection of the frequency and amplitude of the ultrasonic energy used is advantageous in achieving delivery of the ultrasonic energy to the wound wherein the ultrasonic energy has an intensity capable of achieving a therapeutic effect to the wound. Preferably, the radiation surface 36 has a relatively large diameter. Actual selection of the diameter is dependent upon the frequency and amplitude selected. Furthermore, the shape of the radiation surface 36 is selected from one of flat, concave, convex, or a combination thereof, and from the configurations shown in FIGS. 8*a*-8*i*, or a combination thereof.

In another embodiment, ultrasonic energy is delivered to the wound without the use of the spray, i.e., the ultrasonic energy is delivered through a medium other than a spray, including a gaseous medium, such as pure air, e.g., ambient air, where the ultrasound transducer 6 is positioned at a non-contact distance from the wound for providing a therapeutic and beneficial effect. The ultrasound waves, even without the use of a spray, destroy surface bacteria and stimulate health cell growth. This method of wound treatment is particularly advantageous on wounds for which contact with the wound should be avoided.

Figure 10:
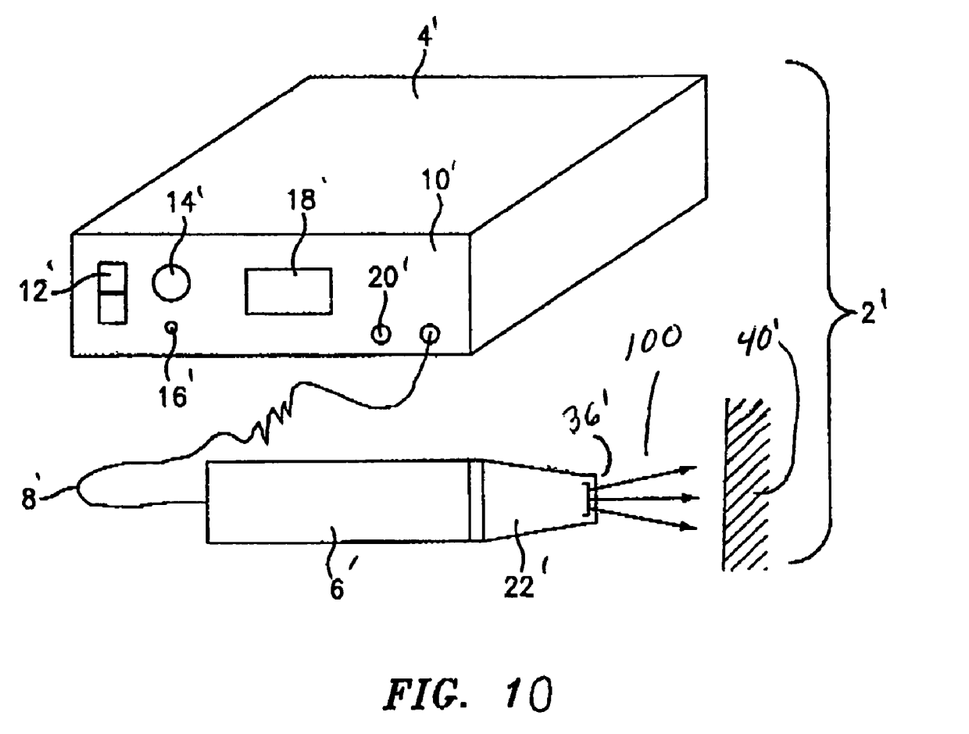
FIG. 10 is a schematic representation of a method of delivery of ultrasonic energy delivered through a gaseous medium, accordance with another embodiment of the present invention.

With reference to FIG. 10, an ultrasonic treatment system 2' is shown including an ultrasound generator 4' connected to an ultrasound transducer 6' by a cable 8' for generating ultrasound energy. Transducer 6' has a radiation surface 36' from which the ultrasound energy is emitted and directed to wound 40'. The generator 4', which is conventional, may have a front panel 10' with a power button 12', a timer 14', a control button 16', a display 18', and one or more jacks 20', for example, for connecting a footswitch. Arrows 100 represent the direction of ultrasound energy generated and directed toward wound 40'. Unlike the above embodiments, a liquid or powder is not contacted with the ultrasonic transducer for generating a spray and directing it to the wound 40'. The ultrasonic energy is delivered through a medium other than a spray, including a gaseous medium, such as pure air ("dry" approach). A horn of the transducer 6' may be configured in accordance with the embodiments shown in FIGS. 7*a*-*g*, 8*a*-*i* and/or 9*a*-*c*.

In a preferred embodiment of the invention, wherein the ultrasonic energy is delivered to the wound 40' through a gaseous medium, such as pure air, for achieving a therapeutic effect at the wound 40', the frequency of the ultrasonic energy generated is selected to be a low frequency. By using a low frequency, a particular or predetermined amplitude for the generated ultrasonic energy is achieved, which is capable of being delivered to the wound with an intensity capable of providing a therapeutic effect to the wound 40', exerting acoustic pressure and/or causing micro-cavitation. Preferably, the amplitude achieved by the ultrasonic energy is at least 3 microns and preferably at least 10 microns. Preferably, the frequency used is in the range of 20 kHz-50 MHz, wherein a preferred range is 20-200 kHz, a more preferred range is 20-40 kHz and a most preferred value is 40 kHz, wherein most preferably the lower limit of the frequency used is outside of the human hearing range.

Furthermore, it is advantageous to use a radiation surface 36' having a shape and size selected to achieve delivery of the ultrasonic energy to the wound where the delivered ultrasonic energy has an intensity capable of providing a therapeutic effect to the wound. Selection of the shape and size of the radiation surface 36' in combination with selection of the frequency and amplitude of the ultrasonic energy used is advantageous in achieving delivery of the ultrasonic energy to the wound wherein the ultrasonic energy has an intensity capable of achieving a therapeutic effect to the wound. Preferably, the perimeter of the radiation surface 36' is round, rectangular, elliptical, oval, spherical, conical, curved, stepped, with chamfer, etc., or a combination thereof, as shown in FIGS. 8(*a*) to 8(*n*), and has a relatively large diameter. Actual selection of the diameter is dependent upon the frequency and amplitude selected. Furthermore, the shape of the radiation surface 36' is selected from one of flat, concave, convex, and a combination thereof.

Figure 11:
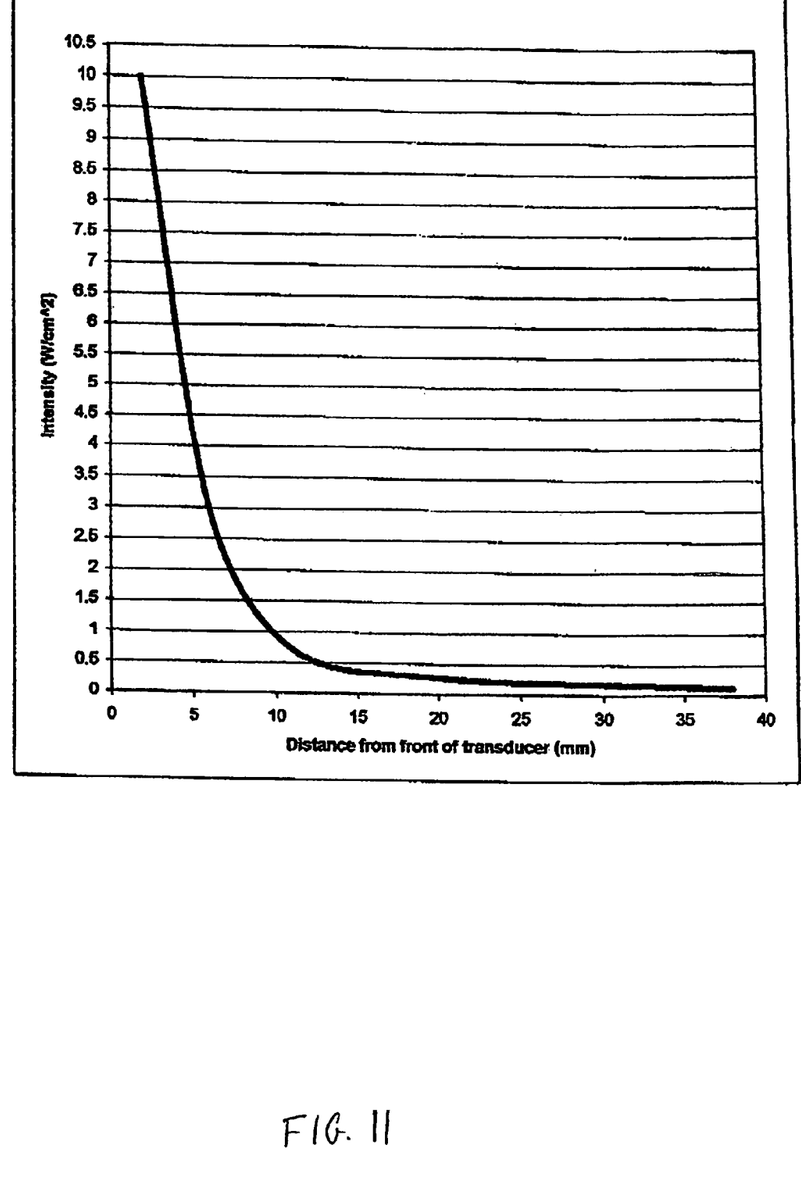
FIG. 11 is a plot of experimental results achieved upon delivering ultrasound energy substantially through a gaseous medium to a wound in accordance with the present invention.

With respect to FIG. 11, results are shown of experimentation at Celleration Acoustic Laboratory, Eden Prairie, Minn. Ultrasonic energy having an intensity capable of providing a therapeutic effect was delivered through air (no spraying of liquid or powder) to a wound using an ultrasound transducer positioned at a non-contact distance from the surface of the wound, as shown by FIG. 10. The ultrasonic energy was generated at a frequency of 40 kHz and an amplitude of 61 microns. The transducer radiation surface was flat, rounded and had a diameter of 1 cm. Hydrophone model number PVDF-Z44-1000 and hydrophone amplifier model number A17db, both manufactured by ONDA Corporation, Sunnyvale, Calif., were employed, using an amplifier gain of 7.44. As shown, with the transducer positioned at a distance of between 2.5 mm and 38 mm from a wound, ultrasonic energy was delivered to the wound having an intensity capable of providing a therapeutic effect to the wound; the intensity being within the range of from 0.1 $W/cm^2$ to 10 $W/cm^2$.

With respect to FIGS. 10-11, the ultrasound energy is delivered to the wound or tissue being treated through a medium other than a spray, including a gaseous medium, such as pure air, e.g., ambient air, including without the use of the spray. Accordingly, the ultrasound energy is delivered to the tissue through a substantial expanse of a substantially purely gaseous medium, such as ambient air. Preferably, the transducer may be positioned at a non-contact distance from the tissue, where the space between the transducer and the tissue through which the ultrasound energy is delivered is an expanse of a substantially purely gaseous medium spanning a distance of at least about 0.1 in. (2.5 mm) from the transducer to the tissue. Preferably the distance spanned is from about 0.1 in. (2.5 mm) to 20 in. (51 cm), and is more preferably from about 0.1 in. (2.5 mm) to 5 in. (12.7 cm).

The embodiment shown in FIGS. 2-6 may further be used for delivering ultrasound energy to the skin without the use of a spray by not providing a liquid within the reservoir 32 so that liquid does not flow to the radiation surface 36, or by selectively controlling delivery of liquid from the reservoir to the radiation surface 36 in accordance with one or more requests from an operator and/or a control module. The operator may make a request via a selection device which may be mechanical and/or electrical, e.g., a button, trigger, lever and/or user interface. The request may be processed mechanically and/or electrically (by analog and/or digital processing) for mechanically controlling flow of the liquid, such as by controlling the valve 34 to remain open or closed or sequentially open and close, in any order. Accordingly, non-contact ultrasound treatment without a spray may be provided to tissue using either the embodiment shown in FIGS. 1-6 or the embodiment shown in FIG. 10.

As described further below, the reservoir may be provided in a device separate from the transducer and the spray may be generated and delivered from another device separate from the transducer, where the separate device may be detached from or attached to the transducer. The spray from the separate device may be a spray generated and delivered by another transducer or by a device that does not use ultrasound energy. Similar to the embodiment described with respect to FIGS. 1-6 in which the spray is delivered simultaneously with delivery of the ultrasound energy, the spray delivered from a separate device may be delivered simultaneously with delivery of the ultrasound energy. Alternatively, the spray may be delivered prior to delivery of the ultrasound energy, as described further below. Furthermore, a treatment may include a series of continual and/or intermittent treatments, wherein individual treatments of the series of treatments are selected from the group consisting of: delivery of ultrasound energy with the use of a spray, i.e., the wet approach as described with respect to FIGS. 1-6; and delivery of ultrasound energy through a medium other than a spray (i.e., a gaseous medium), i.e., the dry approach as described with respect to FIG. 10, with the two or more steps performed in any order. Accordingly, non-contact ultrasound treatment with or without a spray may be provided to tissue using either using the embodiment described with respect to FIGS. 1-6 or the embodiment shown in FIG. 10.

The liquid or powder to be sprayed (via the reservoir 32, valve 34 and radiation surface 36 shown in FIGS. 1-6 or via a separate device) may be an analgesic, such as for use as a local anesthetic, such as prior to a dental procedure, suturing, or other invasive or noninvasive procedure or for relief of pain. The analgesic is sonicated, providing a more immediate effect, a more potent effect, further penetration into the skin, improved precision of dosage, and a more targeted affect for minimizing effects to untargeted tissue. Moreover, independent of the effect of the sonicated analgesic, the low frequency ultrasonic waves applied in accordance with a method of the present invention, such as through the medium of a spray formed from a saline solution, provide an analgesic effect. The combination of the sonicated analgesic and of the low frequency ultrasonic waves in accordance with a method of the present invention produce a strong local anesthetic effect not found in mere topical application of analgesics.

Another embodiment of a method of the invention includes the step of providing a substance, such as a medicament and herein referred to as medicament, for application of the medicament to tissue, and delivering ultrasound energy to the medicament as it is applied or once it is applied and to the tissue using the embodiment shown in FIGS. 1-6 or the embodiment shown in FIG. 10, and the amplitude, frequency, non-contact distance and other parameters for the ultrasound energy, generator and transducer described above. The ultrasound energy is delivered by a non-contact delivery (i.e., without contacting the transducer 6 or 6' to the tissue) to the tissue, as described above, and may be delivered through a spray or without a spray, e.g., by delivering the ultrasound energy through a medium other than a spray, such as ambient air, gas, etc. The medicament is, for example, an antibiotic, an ointment, cream, gel, liquid, salve, oil, saline solution, distilled, non-distilled and/or boiled water, powder, spray, antibacterial agent, antiseptic agent, insulin, analgesic agent, conditioner, surfactant, emollient, or other active ingredient, or a combination thereof.

The medicament may be applied directly to the tissue before the ultrasound energy is delivered to the tissue, and/or during the delivery of the ultrasound energy to the tissue. The medicament may be provided within at least one container from which the medicament is applied to the tissue, where the container is in contact with the tissue, proximate the tissue and/or spaced from the tissue and oriented for directing the medicament at the tissue. The container may have a permeable wall(s) through which the medicament may pass directly to or towards the tissue, manually, automatically and/or mechanically, and/or through which the ultrasound energy may penetrate. The container may be integrated with or separated from the housing of the transducer 6 or 6'. Furthermore, the medicament may be applied below the tissue in addition to or instead of to the surface of the tissue.

The various medicaments and methods for applying the medicament to the tissue may be used sequentially in any combination or sequence in conjunction with application of the ultrasound energy (delivered with and/or without the spray, or sequentially with and without the spray in any sequence). The sequence may include wait periods during which the ultrasound energy is not applied. Specifically, a treatment may include a series of treatments, wherein individual treatments of the series of treatments are selected from the group consisting of: the treatment including the steps of delivering ultrasonic energy from a non-contact distance to the tissue simultaneous with delivery of a spray to the tissue, wherein the ultrasonic energy has an intensity capable of penetrating the tissue to a beneficial depth to provide a therapeutic effect to the tissue and sonicating the spray for causing the medicament to penetrate the tissue to a beneficial depth to provide a therapeutic effect to the tissue; the treatment including the steps of delivering ultrasonic energy from a non-contact distance to the tissue through a substantial expanse of a substantially purely gaseous medium to the tissue, wherein the ultrasonic energy has an intensity capable of penetrating the tissue to a beneficial depth to provide a therapeutic effect to the tissue; and the treatment including the steps of the method of the invention, wherein a different medicament is applied.

Delivery of the ultrasound energy to the medicament and to the tissue energizes the medicament via sonication and causes penetration of the medicament into the tissue for providing an enhanced therapeutic effect to the tissue. Further, the delivery of the ultrasound energy causes exertion of acoustic pressure. The sonicated medicament and the combination of the sonicated medicament and the low frequency ultrasound waves each provide at least advantages similar to the advantages provided by the sonicated spray and the combination of the sonicated spray and low frequency ultrasound waves. Such advantages include increasing potency of the medicament, obtaining more immediate results, decreasing the volume of the medicament used relative to a volume used for a comparable treatment using traditional methods for achieving the same effect, increased precision of dosage of the medicament, re-establishment of traditional antibiotics to which bacteria have become resistant and deeper penetration into the tissue.

The substance may be applied to surfaces other than tissue for non-medical applications, such as cleansing, sterilizing and coating surfaces of objects and food.

The preceding specific embodiments are illustrative of the practice of the invention. It is to be understood, however, that other expedients known to those skilled in the art or disclosed herein, may be employed without departing from the spirit of the invention or the scope of the appended claims.

What is claimed is:

1. A method for treating tissue using ultrasonic energy comprising the steps of:
    applying a medicament to tissue before applying ultrasonic energy; and
    delivering ultrasonic energy from a non-contact distance from the tissue and the medicament to the medicament and to the tissue, wherein the ultrasonic energy is delivered simultaneously with delivery of a liquid spray and the ultrasonic energy has intensity capable of penetrating the tissue to a beneficial depth to provide a therapeutic effect to the tissue, and wherein the ultrasonic energy sonicates the medicament and causes the medicament to penetrate the tissue to a beneficial depth to provide a therapeutic effect to the tissue.

2. The method according to claim 1, further including the step of generating the ultrasonic energy with a particular amplitude indicative of an intensity capable of achieving the therapeutic effect.

3. The method according to claim 2, further including the step of generating the ultrasonic energy with a frequency capable of achieving the particular amplitude.

4. The method according to claim 3, wherein the frequency is in the range of 20 kHz-5 MHz.

5. The method according to claim 3, wherein the frequency is in the range of 20-200 kHz.

6. The method according to claim 3, wherein the frequency is in the range of 20-40 kHz.

7. The method according to claim 2, wherein the particular amplitude is at least 3 microns.

8. The method according to claim 2, wherein the particular amplitude is at least 10 microns.

9. The method according to claim 1, wherein the applying step is performed prior to the delivery step.

10. The method according to claim 1, wherein the applying step is performed during the delivering step.

11. The method according to claim 1, wherein the steps of the method are included in a series of treatments wherein another treatment of the series of treatments is selected from the group consisting of:
    the treatment including the steps of delivering ultrasonic energy from a non-contact distance to the tissue simultaneous with delivery of a spray to the tissue, wherein the ultrasonic energy has an intensity capable of penetrating the tissue to a beneficial depth to provide a therapeutic effect to the tissue and sonicating the spray for causing the spray to penetrate the tissue to a beneficial depth to provide a therapeutic effect to the tissue;
    the treatment including the steps of delivering ultrasonic energy from a non-contact distance to the tissue through a substantial expanse of a substantially purely gaseous medium to the tissue, wherein the ultrasonic energy has an intensity capable of penetrating the tissue to a beneficial depth to provide a therapeutic effect to the tissue; and
    the treatment including the steps of the method of the invention, wherein a different medicament is applied.

12. The method according to claim 1, wherein the medicament is selected from at least one member of the group consisting of: an antibiotic, an ointment, cream, gel, liquid, salve, oil, powder, antibacterial agent, antiseptic agent, insulin, analgesic agent, conditioner, surfactant, emollient, or other active ingredient.

13. The method according to claim 1, wherein the step of delivering includes the step of providing means for delivering the ultrasonic energy at a distance from 2.5 mm-51 cm from the tissue and the medicament.

14. The method according to claim 1, wherein the therapeutic effect is selected from at least one member of the group consisting of increasing blood flow to the tissue, providing a local anesthetic effect and stimulating cell growth.

15. The method of claim 1, wherein the liquid spray includes a medicament.

16. A method for treating a wound comprising the steps of:
    applying a medicament to a wound before applying ultrasonic energy;
    providing a transducer having a distal radiation surface for generating and emitting ultrasonic energy;
    introducing a liquid to the distal radiation surface to produce a spray; and
    delivering the generated and emitted ultrasonic energy to the wound through the spray from a non-contact distance from the surface of the wound and from the medicament applied to the wound, wherein the generated and emitted ultrasonic energy penetrates the wound tissue to a beneficial depth to provide a therapeutic effect for decreasing the healing time for the wound, and wherein the non-contact distance is at least 2.5 mm from the surface of the wound.

17. The method according to claim 16, wherein the generating step includes generating the ultrasonic energy with a particular amplitude indicative of an intensity capable of achieving the therapeutic effect.

18. The method according to claim 17, wherein the generating step further includes the step of generating the ultrasonic energy with a frequency capable of achieving the particular amplitude.

19. The method according to claim 18, wherein the frequency is in the range of 20 kHz-5 MHz.

20. The method according to claim 18, wherein the frequency is in the range of 20-200 kHz.

21. The method according to claim 18, wherein the frequency is in the range of 20-40 kHz.

22. The method according to claim 16, wherein said distal radiation surface has a surface area dimensioned for achieving delivery of the ultrasonic energy to the wound with an intensity capable of achieving the therapeutic effect.

23. The method according to claim 16, wherein said distal radiation surface has a rounded perimeter for achieving delivery of the ultrasonic energy to the wound with an intensity capable of achieving the therapeutic effect.

24. The method according to claim 16, wherein one or more of the following features of the distal radiation surface are selected to achieve delivery of ultrasonic energy to the wound with an intensity capable of achieving the therapeutic effect: a size of a surface area of the distal radiation surface or a shape of a peripheral boundary of the distal radiation surface.

25. The method of claim 16, wherein one or more of the following features of the distal radiation surface are selected to achieve the therapeutic effect: a size of a surface area of the distal radiation surface, a shape of a peripheral boundary of the distal radiation surface, a shape of the curvature of the distal radiation surface selected from one of flat, concave, convex and a combination thereof.

26. The method according to claim 16, wherein the radiation surface is positioned from 2.5 mm-51 cm from the surface of the wound.

27. The method according to claim 16, wherein the generating step includes the steps of generating the ultrasonic energy with a constant or modulated frequency having a wave form selected from the group consisting of sinusoidal, rectangular, trapezoidal, and triangular wave forms.

28. The method according to claim 16, wherein the liquid does not include a medicament.

29. The method according to claim 16, wherein the medicament penetrates the wound to a beneficial depth to provide a therapeutic effect to the wound.

30. The method according to claim 29, wherein the medicament is selected from one or more members of the group consisting of: an antibiotic, an ointment, cream, gel, liquid, salve, oil, powder, antibacterial agent, antiseptic agent, insulin, analgesic agent, conditioner, surfactant, emollient, or other active ingredient.

31. The method according to claim 16, wherein the medicament is selected from at least one member of the group consisting of: an antibiotic, an ointment, cream, gel, liquid, salve, oil, powder, antibacterial agent, antiseptic agent, insulin, analgesic agent, conditioner, surfactant, emollient, or other active ingredient.

32. The method according to claim 16, wherein the therapeutic effect is selected from one or more members of the group consisting of increasing blood flow to the tissue, providing a local anesthetic effect and stimulating cell growth.

33. The method of claim 16, wherein the medicament is applied before the ultrasonic energy is delivered to the wound.

34. The method of claim 16, wherein the medicament is applied during delivery of the ultrasonic energy to the wound.

35. The method of claim 16, wherein the liquid includes a medicament.

36. A method for treating a wound comprising the steps of:
applying a medicament to a wound before applying ultrasonic energy;
generating ultrasonic energy having a particular amplitude and a particular frequency; and
delivering the generated ultrasonic energy to the wound through a liquid spray from a non-contact distance from the medicament and from the surface of the wound, wherein the generated ultrasonic energy penetrates the wound tissue to a beneficial depth to provide a therapeutic effect for decreasing the healing time for the wound, wherein the particular amplitude is indicative of an intensity capable of achieving the therapeutic effect, and wherein the non-contact distance is at least 2.5 mm from the surface of the wound.

37. The method according to claim 36, wherein the particular amplitude is at least 3 microns.

38. The method according to claim 36, wherein the particular amplitude is at least 10 microns.

39. The method of claim 36, wherein the liquid spray does not include a medicament.

40. The method according to claim 36, wherein the medicament penetrates the wound to a beneficial depth to provide a therapeutic effect to the wound.

41. The method according to claim 40, wherein the medicament is selected from one or more members of the group consisting of: an antibiotic, an ointment, cream, gel, liquid, salve, oil, powder, antibacterial agent, antiseptic agent, insulin, analgesic agent, conditioner, surfactant, emollient, or other active ingredient.

42. The method according to claim 36, wherein the medicament is selected from at least one member of the group consisting of: an antibiotic, an ointment, cream, gel, liquid, salve, oil, powder, antibacterial agent, antiseptic agent, insulin, analgesic agent, conditioner, surfactant, emollient, or other active ingredient.

43. The method according to claim 36, wherein the step of delivering includes the step of providing means for delivering the ultrasonic energy at a distance from 2.5 mm-51 cm from the wound.

44. The method according to claim 36, wherein the therapeutic effect is selected from one or more members of the group consisting of increasing blood flow to the tissue, providing a local anesthetic effect and stimulating cell growth.

45. The method of claim 36, wherein the medicament is applied before the ultrasonic energy is delivered to the wound.

46. The method of claim 36, wherein the medicament is applied during delivery of the ultrasonic energy to the wound.

47. The method of claim 36, wherein the liquid spray includes a medicament.

* * * * *